United States Patent
Rousseau

(10) Patent No.: US 8,632,488 B2
(45) Date of Patent: Jan. 21, 2014

(54) FLUID FILLED IMPLANTS FOR TREATING MEDICAL CONDITIONS

(75) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 660 days.

(21) Appl. No.: 12/638,492

(22) Filed: Dec. 15, 2009

(65) Prior Publication Data
US 2011/0144558 A1    Jun. 16, 2011

(51) Int. Cl.
*A61M 5/00*    (2006.01)
*A61F 2/06*    (2013.01)

(52) U.S. Cl.
USPC ............................ 604/9; 623/1.14; 623/1.17

(58) Field of Classification Search
USPC ............ 604/8–10; 623/1.14, 1.15, 1.17, 1.18, 623/1.2, 1.22, 1.25
See application file for complete search history.

(56) References Cited

U.S. PATENT DOCUMENTS

| | | | |
|---|---|---|---|
| 3,123,077 A | 3/1964 | Alcamo | |
| 3,378,010 A | 4/1968 | Codling et al. | |
| 4,069,825 A | 1/1978 | Akiyama | |
| 4,290,763 A * | 9/1981 | Hurst | 493/341 |
| 4,557,264 A | 12/1985 | Hinsch | |
| 4,839,215 A | 6/1989 | Starling et al. | |
| 4,881,939 A | 11/1989 | Newman | |
| 4,950,285 A | 8/1990 | Wilk | |
| 5,053,047 A | 10/1991 | Yoon | |
| 5,123,913 A | 6/1992 | Wilk et al. | |
| 5,269,783 A | 12/1993 | Sander | |
| 5,284,161 A | 2/1994 | Karell | |
| 5,311,028 A | 5/1994 | Glavish | |
| 5,393,984 A | 2/1995 | Glavish | |
| 5,483,077 A | 1/1996 | Glavish | |
| 5,484,444 A | 1/1996 | Braunschweiler et al. | |
| 5,609,559 A | 3/1997 | Weitzner | |
| 5,683,417 A | 11/1997 | Cooper | |
| 5,704,895 A | 1/1998 | Scott et al. | |
| 5,792,067 A | 8/1998 | Karell | |

(Continued)

FOREIGN PATENT DOCUMENTS

| | | |
|---|---|---|
| CN | 2465680 | 12/2001 |
| CN | 102198010 | 9/2011 |

(Continued)

OTHER PUBLICATIONS

Harries et al., "The Surgical treatment of snoring", Journal of Laryngology and Otology, pp. 1105-1106 (1996).

(Continued)

*Primary Examiner* — Melanie Hand

(57) ABSTRACT

An implant for treating medical disorders includes a first chamber having a flexible outer layer that surrounds a flexible inner layer, a second chamber in communication with the first chamber, and a fluid transfer assembly adapted for transferring fluid between the second chamber and the first chamber for selectively modifying the rigidity of the first chamber. The implant includes at least one restraining element in contact with the flexible outer and inner layers for at least partially restricting volume expansion of the first chamber as the fluid is transferred into the first chamber. The first chamber is adapted to become more rigid as the fluid is transferred into the first chamber and more flexible as the fluid is removed from the first chamber. The first chamber is implantable within the soft tissue of a patient such as a tongue, soft palate, pharyngeal wall, urinary tract, rectum, trachea, or stomach.

24 Claims, 13 Drawing Sheets

(56) References Cited

U.S. PATENT DOCUMENTS

| | | |
|---|---|---|
| 5,843,077 A | 12/1998 | Edwards |
| 5,931,855 A | 8/1999 | Buncke |
| 6,161,541 A | 12/2000 | Woodson |
| 6,241,747 B1 | 6/2001 | Ruff |
| 6,250,307 B1 | 6/2001 | Conrad et al. |
| 6,348,156 B1 | 2/2002 | Vishnoi et al. |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 2001/0037133 A1 | 11/2001 | Knudson et al. |
| 2003/0004579 A1 | 1/2003 | Rousseau et al. |
| 2003/0034312 A1 | 2/2003 | Unger et al. |
| 2003/0149445 A1* | 8/2003 | Knudson et al. .............. 606/196 |
| 2003/0149447 A1 | 8/2003 | Morency et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1 | 11/2004 | Fierro |
| 2005/0038472 A1 | 2/2005 | Furst |
| 2005/0082452 A1 | 4/2005 | Kirby |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze et al. |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1 | 11/2006 | Atkinson et al. |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison |
| 2009/0165803 A1 | 7/2009 | Bhat et al. |
| 2010/0023055 A1 | 1/2010 | Rousseau |
| 2010/0024830 A1 | 2/2010 | Rousseau |
| 2010/0030011 A1 | 2/2010 | Rousseau et al. |
| 2010/0037901 A1 | 2/2010 | Rousseau et al. |
| 2010/0080791 A1 | 4/2010 | Rousseau et al. |
| 2010/0106246 A1 | 4/2010 | Rousseau |
| 2010/0108077 A1 | 5/2010 | Lindh |
| 2010/0132719 A1 | 6/2010 | Jacobs et al. |
| 2010/0137794 A1 | 6/2010 | Knudson |
| 2010/0137905 A1 | 6/2010 | Weadock et al. |
| 2010/0163056 A1 | 7/2010 | Tschopp |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0294284 A1 | 11/2010 | Hohenhorst et al. |
| 2010/0319710 A1 | 12/2010 | Sharkaway et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |

(56) References Cited

U.S. PATENT DOCUMENTS

| | | |
|---|---|---|
| 2011/0178439 A1 | 7/2011 | Irwin et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |

FOREIGN PATENT DOCUMENTS

| | | |
|---|---|---|
| DE | 10245076 | 4/2004 |
| EP | 2145587 | 1/2010 |
| EP | 2517633 | 10/2012 |
| FR | 2651113 | 3/1991 |
| JP | 2003265621 | 9/2003 |
| SU | 927236 | 5/1982 |
| WO | 9900058 | 1/1999 |
| WO | 0066050 | 11/2000 |
| WO | WO 01/21107 A1 | 3/2001 |
| WO | 03096928 | 11/2003 |
| WO | 2004020492 | 3/2004 |
| WO | 2004021869 | 3/2004 |
| WO | 2004021870 | 3/2004 |
| WO | 2004060311 | 7/2004 |
| WO | 2004084709 | 10/2004 |
| WO | 2005046554 | 5/2005 |
| WO | 2005051292 | 6/2005 |
| WO | 2005082452 | 9/2005 |
| WO | 2005122954 | 12/2005 |
| WO | 2006012188 | 2/2006 |
| WO | 2006072571 | 7/2006 |
| WO | 2006108145 | 10/2006 |
| WO | 2007056583 | 5/2007 |
| WO | WO 2007/075394 A2 | 7/2007 |
| WO | 2007132449 | 11/2007 |
| WO | 2007134005 | 11/2007 |
| WO | 2007146338 | 12/2007 |
| WO | 2007149469 | 12/2007 |
| WO | 2008118913 | 10/2008 |
| WO | 2009023256 | 2/2009 |
| WO | 2009036094 | 3/2009 |
| WO | 2010019376 | 2/2010 |
| WO | 2010035303 | 4/2010 |
| WO | 2010065341 | 6/2010 |
| WO | 2012041205 | 4/2012 |
| WO | 2012064902 | 5/2012 |
| WO | 2012170468 | 12/2012 |

OTHER PUBLICATIONS

Wassmuth et al., "Cautery-assisted palatal stiffening operation for the treatment of obstructive sleep apnea syndrome", Otolaryngology - Head and Neck Surgery, vol. 123 (1), pp. 55-60 (2000).
The Pillar Palatal Implant System, Restore Medical, Inc., www.restoremedical.com, 2 pp. (2008).
Repose Genioglossus Advancement, INFLUENT Medical, www.influ-ent.com, 1 page. (2008).
Cole et al., "Snoring: A Review and a Reassessment", J. of Otolaryngology, pp. 303-306 (1995).
Huang et al., "Biomechanics of snoring", Endeavour, vol. 19(3): pp. 96-100 (1995).
Pang, Kenny et al., "Tongue Suspension Suture in Obstructive Sleep Apnea", Operative Techniques in Otolaryngology, vol. 17, No. 4, Dec. 2006, pp. 252-256.
Schwab et al., "Upper airway and soft tissue changes induced by CPAP in normal subject", Am. J. Respit. Crit. Care Med., vol. 154, No. 4, Oct. 1996, pp. 1106-1116.
Schwartz et al., "Effects of electrical stimulation to the soft palate on snoring and obstructive sleep apnea", J. Prosthetic Dentistry, pp. 273-281 (1986).
Shamsuzzaman et al., "Obstructive Sleep Apnea; Implications for Cardiac and Vascular Disease", JAMA vol. 290 (14); pp. 1906-1914.
Teles et al., "Use of Palatal Lift Prosthesis on Patient Submitted to Maxillectomy: A Case Report", Applied Cancer Res. 2005, vol. 25(3), pp. 151-154.
The Advance System, Aspire Medical, Inc. www.aspiremedical.com, 3 pp. (2008).
Vicente et al., "Tongue-Base Suspension in Conjunction with Uvulopapatopharyngoplasty for Treatement of Severe Obstructive Sleep Apnea: Long-term Follow-Up Results", The Laryngoscope, vol. 115(7), pp. 1223-1227 (2006).
Wiltfang et al., "First results on daytime submandibular electrostimulation of suprahyoidal muscles to prevent night-time hypopharyngeal collapse in obstructive sleep apnea syndrom", Intl J. of Oral & Maxillofacial Surgery, pp. 21-25 (1999).
Notification of Transmittal of the International Search Report and the Written Opinion of the International Search Authority or the Declaration mailed on Feb. 3, 2010; PCT/US2009/051921; International Filing Date: Jul. 28, 2009.
Notification of Transmittal of the International Search Report and the Written Opinion of the International Search Authority or the Declaration mailed on May 25, 2010; PCT/US2010/023152; International Filing Date: Apr. 2, 2010.
International Search Report dated Nov. 4, 2009 for International Patent Application No. PCT/US2009/052126.
International Search Report dated Dec. 21, 2009 for International Patent Application No. PCT/US2009/057661.
International Search Report dated Dec. 22, 2009 for International Patent Application No. PCT/US2009/061223.
International Search Report dated Apr. 29, 2010 for International Patent Application No. PCT/US2009/065293.
U.S. Appl. No. 12/182,402, filed Jul. 30, 2008.
U.S. Appl. No. 12/183,955, filed Jul. 31, 2008.
U.S. Appl. No. 13/247,713, filed Sep. 28, 2011.
U.S. Appl. No. 13/279,384, filed Oct. 24, 2011.
U.S. Appl. No. 13/314,704, filed Dec. 8, 2011.
Schleef et al., "Cytokine Activation of Vascular Endothelium, Effects on Tissue-Type 1 Plasminogen Activator Inhibitor", The J. of Biological Chem., vol. 263, No. 12, pp. 5797-5803 (1988).
International Search Report dated Dec. 29, 2009 for International Patent Application No. PCT/US2009/061455.
International Search Report dated Jan. 21, 2010 for International Patent Application No. PCT/US2009/052110.
International Search Report dated May 25, 2010 for International Patent Application No. PCT/US2010/025778.
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
Database WPI Week 198312, Thomson Scientific, London, GB; AN 1983-D9513K XP002693421, -& SU 927 236 A1 (Petrozazodsk Unive) May 15, 1982 abstract (see figures 7 & 8).
International Search Report dated May 25, 2010 for International Patent Application No. PCT/US2010/023152.
International Search Report dated Apr. 9, 2013 for International Patent Application No. PCT/US2012/061569.
International Search Report dated Apr. 2, 2013 for International Patent Application No. PCT/US2012/067708.
Written Opinion dated Nov. 27, 2012 for International Patent Application No. PCT/US2012/056577.

* cited by examiner

FLUID FILLED IMPLANTS FOR TREATING MEDICAL CONDITIONS

CROSS REFERENCE TO RELATED APPLICATIONS

The present application is related to commonly assigned U.S. patent application Ser. No. 12/608,057, filed on Oct. 29, 2009, the disclosure of which is hereby incorporated by reference herein.

BACKGROUND OF THE INVENTION

1. Field of the Invention

The present invention generally relates to implants for treating medical disorders, and more specifically relates to fluid filled implants and related methods for treating patients suffering from medical disorders.

2. Description of the Related Art

Fluid filled implants have been used for treating a broad range of medical disorders. For example, U.S. Pat. No. 4,881,939 to Newman discloses an implantable, inflatable helical cuff that is wrapped around a tubular body member such as a nerve cord, esophagus, colon, intestine, or blood vessel in a pressure transferring relationship. The cuff may be inflated to function as an occluder, or partially inflated to function as a pressure sensor or transducer in a medical system.

U.S. Pat. No. 5,609,559 to Weitzner discloses an intravaginal device for female patients to prevent involuntary loss of urine. The device includes an anterior inflatable body having a hose extending therefrom and a pressure application zone structured and disposed to direct pressure against the urethra and urethra vesicle junction when inflated, to thereby prevent loss of urine. A posterior portion extends from the inflatable anterior body, terminating at a distal end, and is structured and configured to promote insertion and passage of the device within the vagina. A source of pressurized air is releasably attachable to a distal end of the hose to facilitate inflation of the anterior body U.S. Patent Application Publication No. 2006/0241339 discloses an implantable device and method for restoring continence and controlling coaptivity of a body lumen. The device includes a fill port block which has one or more self-sealing septums. The fill port block is connected to one or more elongated conduits and ultimately to one or more expandable elements for communicating fluid. The one or more expandable elements are implanted and adjusted from a remote location using the fill port block.

U.S. Patent Application Publication No. 2008/0146868 to Robert et al. discloses an implantable male incontinence device, which has an inflatable balloon affixed to a central portion of a reinforced nonextensible elastomeric strip. The balloon includes a first length of elastomeric tubing that provides fluid communication with the interior chamber of the balloon. The uninflated balloon is implanted to overlie the male urethra with the nonextensible strip oriented horizontally and facing away from the urethra. The lateral opposing ends of the nonextensible strip are sutured to the periosteum of respective left and right iliac bones and the inflation port is implanted beneath the skin in an accessible portion of the body, preferably in the scrotum or, less preferably, in the perineum. The inflation port, which also includes a second length of tubing in fluid communication therewith, is implanted beneath the skin and the first and second lengths of tubing are connected to one another. A fluid is injected into the inflation port and directed to the interior chamber of the balloon causing it to inflate and force periurethral tissue against the urethra to partially constrict the urethra and reduce the pressure of urine on the external meatus. The urethral constriction can be adjusted by increasing or decreasing the amount of fluid in the balloon via the inflation port.

All of the above-described implants have inflatable balloons or pouches that expand in volume as fluid is introduced therein. This requires the expandable portions of the implants to be coupled with a relatively large fluid source, which generally increases the overall size of the implant system. The need to introduce a large volume of fluid to expand the implant also increases the amount of effort required from a patient to inflate the implant. Thus, in spite of the above advances, there remains a need for improved fluid-filled implant systems that use less fluid, that are more compact, that are more durable, that require less patient effort, that encourage patient compliance, and that minimize patient discomfort.

SUMMARY OF THE INVENTION

In one embodiment, an implant for treating medical disorders includes a first chamber having a flexible outer layer, a second chamber in communication with the first chamber, and a fluid transfer assembly adapted for transferring fluid between the second chamber and the first chamber for selectively modifying the rigidity of the first chamber. The implant desirably includes at least one restraining element, such as a spot weld, in contact with the flexible outer and inner layers for restricting volume expansion of the first chamber when the fluid is transferred into the first chamber. In one embodiment, the first chamber is preferably adapted to become more rigid as the fluid is transferred into the first chamber and more flexible as the fluid is removed from the first chamber. In one embodiment, the first chamber is preferably adapted to change shape as the fluid is introduced into the first chamber. In one embodiment, the first chamber is preferably more flexible and curved when the fluid is removed from the chamber and becomes more rigid and straighter when the fluid is introduced into the first chamber. In one embodiment, the first chamber may lengthen and become more rigid as the fluid is transferred into the first chamber.

In one embodiment, the implant preferably includes at least one conduit extending between the fluid transfer assembly and the first chamber for transferring the fluid into the first chamber. In one embodiment, the implant may have two or more conduits for transferring fluid.

In one embodiment, the at least one restraining element comprises at least one weld joining opposing surface areas of the flexible layers. The at least one weld may be formed using well-known joining techniques such as heat, pressure and/or adhesive. The at least one weld desirably prevents, restricts, governs, or controls volume expansion of the first chamber in the vicinity of the at least one weld as the fluid is transferred into the first chamber. In one embodiment, the at least one weld preferably includes a plurality of welds joining respective opposing surface areas of the flexible layers. The plurality of welds may be spaced intermittently from one another along the length or area of the first chamber. In one embodiment, the restraining elements minimize volume expansion of the first chamber as fluid is introduced therein so that only the rigidity level and the shape of the first chamber changes as the fluid pressure builds within the first chamber.

In one embodiment, the first chamber is desirably implantable within soft tissue of a patient at any selected angle relative to an anterior-posterior, lateral, vertical, or horizontal axis of the patient. The first chamber may also extend along any of the above-described axes. The implant described herein may be implantable in a number of different locations within a patient for treating various medical disorders. In one embodiment, the first chamber of the implant is implantable within a tongue, a soft palate or a pharyngeal wall for treating obstructive sleep apnea. The first chamber may also be implantable adjacent a rectum or adjacent a bowel of a patient for treating anal or fecal incontinence. The implant may also be utilized for treating swallowing difficulties such as dysphagia such as by placing the first chamber adjacent a pharyngeal wall. The implant may also be positioned adjacent a stomach whereby the first chamber applies pressure to a stomach for minimizing eating disorders. The present invention may also be positioned adjacent or in contact with a urinary tract of a patient for treating symptoms associated with urinary incontinence.

The implant disclosed herein preferably utilizes a fluid such as a liquid, a gas or a combination thereof for providing rigidity, lengthening and/or changing the shape of the first chamber.

In one embodiment, an implant for treating medical disorders includes a first chamber, a second chamber in fluid communication with the first chamber, and a fluid transfer assembly that couples the first and second chambers and that is adapted to transfer fluid therebetween for selectively modifying the rigidity of the flexible chamber. The first chamber is desirably adapted to become more rigid as the fluid is transferred into the first chamber and the fluid pressure within the compartment increases. The implant desirably includes at least one restraining element within the construct of the flexible chamber for restricting expansion of the flexible chamber as the fluid is transferred into the flexible chamber.

In one embodiment, the fluid transfer assembly desirably includes a conduit coupled with the first chamber for transferring the fluid to the first chamber. In one embodiment, the first chamber desirably includes a flexible layer covering a distal end of the conduit. The at least one restraining element desirably includes at least one weld in contact with the flexible layer for restricting volume expansion of the first chamber as the fluid is transferred into the first chamber. In one embodiment, the at least one weld prevents volume expansion of the first chamber as the fluid is transferred into the first chamber.

In one embodiment, an implant for treating medical disorders includes a first chamber having a flexible outer layer, a second chamber in communication with the first chamber, and a fluid transfer assembly for selectively transferring fluid between the first and second chambers. In one embodiment, the first chamber is preferably adapted to become more rigid as the fluid is transferred into the first chamber and more flexible as the fluid is removed from the first chamber. The implant desirably includes at least one restraining element in contact with the first chamber for at least partially restricting volume expansion of the first chamber as the fluid is transferred into the first chamber. In one embodiment, the at least one restraining element desirably includes a plurality of spaced welds that join opposing surfaces of the flexible outer layer together.

In one embodiment, the implant also includes an elongated conduit in communication with the first chamber for supplying the fluid to the first chamber. The at least one restraining element preferably includes at least one weld coupling the flexible outer layer with an outer surface of the elongated conduit. In one embodiment, the at least one restraining element includes a plurality of restraining elements in contact with the flexible outer layer for preventing or limiting volume expansion of the first chamber as the fluid is transferred into the first chamber.

The implants disclosed herein may be placed within any one of a wide range of angles relative to an anterior-posterior axis, a vertical axis, a transverse axis, or a horizontal axis of a patient. In one embodiment, the implant(s) may extend laterally relative to the anterior-posterior axis. In one embodiment, the implant(s) may extend in a direction that is parallel with the anterior-posterior axis. In yet another embodiment, the implant(s) may be placed at an angle that lies between the transverse axis and the anterior-posterior axis position. The implants may also be placed along the vertical axis of a patient, the horizontal axis of a patient, or at any angle between the vertical and horizontal axes. The angle that is selected is preferably chosen to maximize therapeutic benefit for a patient.

In one embodiment, the second chamber and the fluid transfer assembly are implanted at a location within the body that is remote from the first chamber. In one embodiment, the second chamber of the implant and the fluid transfer assembly of the implant are implantable within an inframandibular region of a patient. The fluid reservoir and the fluid transfer assembly may be placed subcutaneously at a remote location from the location of the flexible, first chamber. The implanted fluid transfer assembly, such as a pump and/or a valve assembly, is desirably engageable by a patient for selectively transferring fluid from the second chamber to the first chamber so as to modify the rigidity, flexibility and/or shape of the first chamber. In one embodiment, a patient uses his or her tactile senses to locate the fluid transfer assembly beneath the skin and then manipulates the fluid transfer assembly to physically transfer fluid between the fluid reservoir and the first chamber.

In one embodiment, the implant desirably includes a fluid that is disposable within the first and second chambers of the implant. The fluid may include a liquid or a gas that is selectively transferred back and forth between the first and second chambers for modifying the rigidity, flexibility, length and/or shape of the first chamber.

In one embodiment, the flexible chamber may be produced with an undulating or corrugated tubular structure to facilitate curvilinear deformation of the device in the unstressed condition. In one embodiment, the fluid is passable through the interstices of a corrugated tubular structure to enable the flexible chamber to be readily transformed to a more rigid state while requiring the use of only a minimum quantity of fluid.

In one embodiment, the implant includes a flexible conduit that interconnects and provides fluid communication between the first chamber and the fluid reservoir. The flexible conduit may also provide fluid communication between the fluid transfer assembly and both the first chamber and the fluid reservoir. In one embodiment, the implant may include two or more flexible conduits for forming the fluid communication links described above.

In one embodiment, the first chamber is configured as a straight device that can be deformed into a curvilinear geometry during installation. The deformed first chamber changes into the preferred shape as the fluid is transferred from the second chamber or fluid reservoir to the first chamber and the pressure within the chamber increases. In one embodiment, the first chamber is flexible and is deformed into a slightly curved configuration before the fluid is transferred between the second chamber and the first chamber. In one embodiment, the first chamber may normally be in a flexible configuration. Before the patient takes an action, e.g. urinates, defecates, eats, sleeps, etc., the fluid is transferred to the first chamber so that the first chamber becomes more rigid, changes shape and/or lengthens.

In one embodiment, the flexible, first chamber is desirably formed from either two pieces of film material, such as polymer films, or one piece of film material that is folded onto itself and that is applied to the end of a conduit such as a fluid transfer tube. In one embodiment, the fluid transfer tube is desirably supplied with a closed distal end on the main lumen and a hole in the sidewall of the tube that is in communication with an inner lumen extending along the longitudinal axis of the tube. In one embodiment, an inner layer of film material is desirably shorter than an outer layer of film material. The inner layer is preferably intended to only be fixated about the end of the tube that is distal to the hole in the sidewall of the tube. The inner and outer layers are preferably wrapped around the end of the tube, with the inner layer being bonded to the distal end of the transfer tube. The outer layer is desirably bonded to the proximal side of the hole in the sidewall hole of the transfer tube. In one embodiment, the perimeters of the two inner and outer layers are preferably bonded together to form a sealed chamber between the two layers of film and the free edge is bonded to form a circular cylindrical shape. The formation of the dual wall cylinder enables a reduction in the fluid volume required to enable pressurization of the cylinder as only the compartment between the two layers is filled. In one embodiment, one or more of the inner and outer layers may be in contact with one or more restraining elements (e.g. welds) for preventing, limiting, or controlling volume expansion of the first chamber as fluid is introduced therein.

In one embodiment, at least one part of the implant, and preferably the first chamber, has a surface adapted to promote tissue in-growth. The tissue in-growth promoting surface is desirably selected from a group of outer surfaces including a textured surface, a porous surface, a braided surface, a mesh surface, a fleece surface, and a coating such as hydroxyapatite for inducing bone or tissue in-growth. In one embodiment, the first chamber is made of any of the well-known flexible, durable, biocompatible materials. In one embodiment, the first chamber may be made of any of the well-known biocompatible polymers and biocompatible elastomeric materials. In one embodiment, the first chamber may be made of silicone, latex, polyurethane, nylon, or polyester, fluoropolymers such as polyvinylidene fluoride or combinations thereof.

Although the present invention is not limited by any particular theory of operation, it is believed that the fluid filled implant of the present application provides a number of benefits over prior art devices. First, the fluid filled implant may be removed from a patient if efficacious results are not obtained. Second, the fluid filled implant desirably affects the target tissue when it is pressurized at time periods that are selected by the patient. In one embodiment, a patient may control the rigidity and shape of the fluid filled implant without requiring external devices or appliances. In addition, the fluid filled implant of the present invention preferably changes the shape of tissue without requiring a hard anchoring point thereby minimizing the chance of the implant tearing out or pulling through the tissue. In one embodiment, the fluid filled implant desirably includes a thin walled pressure chamber that is designed to reduce the volume of fluid required to provide significant stiffening of the implant and to reduce the volume of fluid required to be removed from the implant for returning the implant to a flexible condition.

In one embodiment, the implant includes a pressurized cylinder constructed of flexible material. In the event of forceful swallowing during sleep, the implant may deform temporarily to allow swallowing. After the muscular activity related to swallowing subsides, the implant preferably returns to the preferred shaped so as to provide support and re-shaping of the relaxed tongue or tissue of the upper airway.

In one preferred embodiment, a fluid filled implant may be utilized to provide favorable support and re-shaping of an airway upon demand by a patient. In one embodiment, an implant is fabricated from flexible film materials so patients are not aware that the implant is in place. In one embodiment, a pump or valve may be included in-line within two layers of film that have been thermo-formed into a bladder shape on one end and bonded together on the opposing end to provide a "unitary" type construction without requiring extra bonding seams or joints.

These and other preferred embodiments of the present invention will be described in more detail below.

DETAILED DESCRIPTION

Figure 1A:
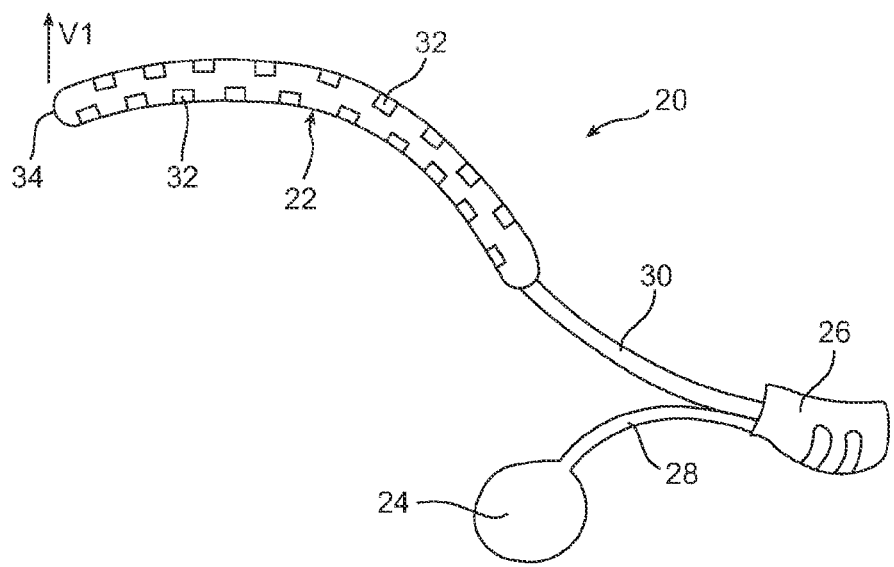
FIG. 1A shows an implant for treating medical disorders including a first chamber, a second chamber and a fluid transfer assembly, in accordance with one embodiment of the present invention.

Referring to FIG. 1A, in one embodiment of the present invention, an implant 20 for treating medical disorders includes a first chamber 22, a second chamber 24 and a fluid transfer assembly 26 for selectively transferring fluid, such as gas or liquid, back and forth between the first and second chambers. The first and second chambers 22, 24 are preferably in communication with one another via the fluid transfer assembly 26. In one embodiment, the first chamber 22 is normally flexible and becomes more rigid, changes shape and/or lengthens when fluid is introduced into the first chamber 22. In one preferred embodiment, the first chamber 22 has limited or no expansion capabilities so that the volume of the first chamber 22 does not significantly change (e.g. expand) as fluid is transferred into the first chamber. As such, only the rigidity, shape and/or length of the first chamber changes as fluid is transferred into the first chamber. In one embodiment, the volume expansion of the first chamber 22 is controlled by restraining elements 32, such as welds or ties, formed along the length of the first chamber. In one embodiment, the first chamber 22 is minimally expandable, which means that the volume of the first chamber does not increase significantly as fluid is introduced into the first chamber. In one embodiment, the second chamber 24 may be expandable.

In one embodiment, the implant 20 preferably includes a first conduit 28 extending between the second chamber 24 and the fluid transfer assembly 26. The first conduit 28 preferably provides fluid communication between the second chamber 24 and the fluid transfer assembly 26 so that fluid may be passed therebetween. The implant 20 also preferably includes a second conduit 30 that desirably extends between the fluid transfer assembly 26 and the first chamber 22 for passing fluid therebetween. In one embodiment, an implant may include a fluid transfer assembly having only a single conduit extending between the first chamber 22 and the second chamber 24, whereby the fluid transfer assembly includes one or more valves and/or pumps provided in the single conduit.

Figure 1B:
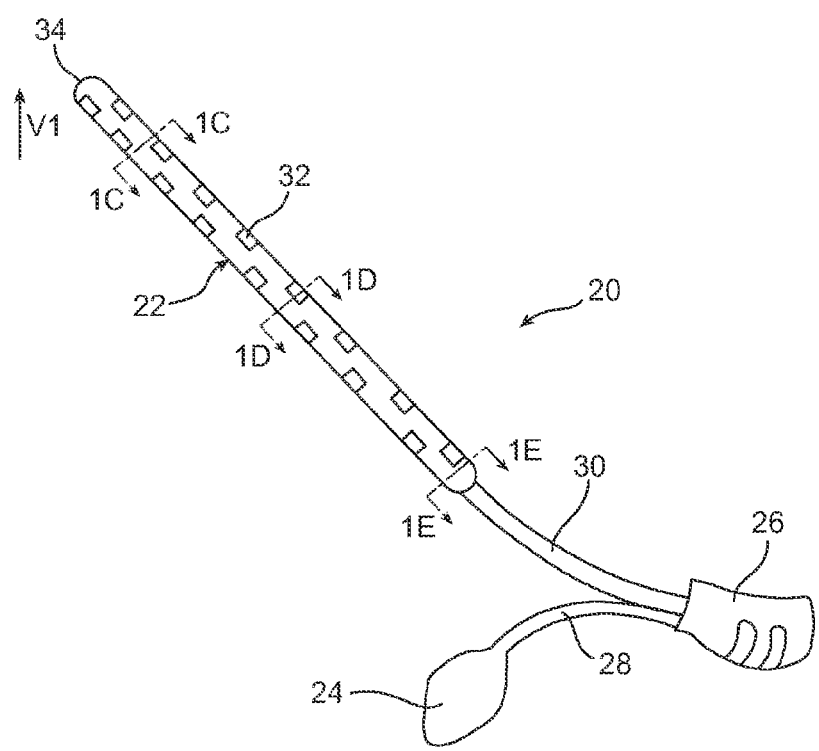
FIG. 1B shows the implant of FIG. 1A after fluid has been transferred from the second chamber to the first chamber, in accordance with one embodiment of the present invention.

Referring to FIG. 1B, in one embodiment, fluid may be selectively extracted from the second chamber 24 and introduced into the first chamber 22 using the fluid transfer assembly 26. In one embodiment, the fluid transfer assembly 26 may be compressed and released so as to draw fluid from the second chamber 24, transfer the fluid through the first and second conduits 28, 30, and introduce the fluid into the first chamber 22. Referring to FIGS. 1A and 1B, as the fluid is transferred from the second chamber 24 to the first chamber 22, the first chamber 22 preferably becomes more rigid, changes shape, and/or lengthens so as to transform the first chamber 22 from the more flexible state shown in FIG. 1A to the more rigid state shown in FIG. 1B. As described herein, in one embodiment, the volume or size of the first chamber undergoes minimal expansion or change as fluid is transferred into the first chamber and the resulting chamber pressure increases. As the first chamber 22 becomes more rigid, the first chamber 22 preferably straightens so that a distal tip 34 of the first chamber 22 moves upwardly in a vertical direction designated $V_1$.

In one embodiment, it may be desirable to return the implant 20 from the more rigid, straighter state shown in FIG. 1B to the more flexible, curved state shown in FIG. 1A. This may be accomplished by engaging the fluid transfer assembly 26, such as a pump and/or a valve, for removing a small volume fluid from the first chamber 22 to depressurize the chamber, and transferring the fluid back to the second chamber 24 or fluid reservoir via the first and second conduits 28, 30. In one embodiment, the fluid transfer assembly 26 is operated to remove the fluid from the first chamber 22, and pass the fluid through the second conduit 30, through the fluid transfer assembly 26, through the first conduit 28, and into the second chamber 24. The fluid transfer may be accomplished through active pumping action of the transfer assembly 26 or through the use of a pressure relief valve located in the transfer assembly. Once the fluid has been returned to the second chamber 24, the first chamber 22 returns to the more flexible, curved state shown in FIG. 1A. The first chamber 22 may be maintained in the more flexible state shown in FIG. 1A until a patient desires to increase the rigidity of the first chamber 22 (e.g. immediately prior to eating, urinating, or sleeping). The patient may repeatedly and selectively change the relative rigidity and/or shape of the first chamber 22 by either introducing fluid into the first chamber 22 or removing fluid from the first chamber 22.

Referring to FIGS. 1A and 1B, in one embodiment, the first chamber 22 may have restraining elements 32, such as welds or joints, that prevent and/or substantially limit expansion of the volume of the first chamber 22 as fluid is introduced into the first chamber. As a result, the first chamber 22 will preferably change shape and/or become more rigid as fluid is introduced therein, but the volume or cross-sectional dimension of the first chamber will not change. In the particular embodiment shown in FIGS. 1A and 1B, the restraining elements 32 are preferably welds that are utilized for limiting and/or preventing volume expansion of the first chamber as fluid is introduced therein. Controlling and/or limiting the volume expansion will preferably provide an implant that becomes straighter and more rigid as fluid is introduced therein without significantly increasing the volume of the first chamber, and using less fluid than is required for prior art expandable implants.

Figure 1C:
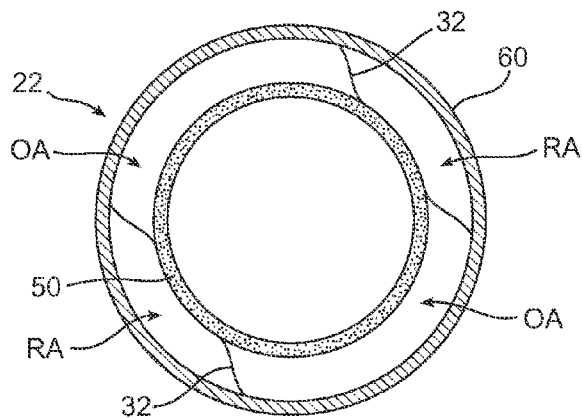
FIG. 1C shows a cross-sectional view of the implant shown in FIG. 1B taken along line 1C-1C thereof.

FIG. 1C shows a cross-sectional view of the first chamber 22 of the implant 20 shown in FIG. 1B. The implant 20 includes the second conduit 30 having a central channel adapted to transport fluid toward the distal end of the second conduit 30 and into the first chamber 22. The first chamber 22 includes a flexible, durable outer layer 60 that surrounds a flexible inner layer 50. In the particular embodiment shown in FIG. 1C, the flexible outer layer 60 that defines the outer perimeter of the first chamber 22 has a substantially cylindrical shape. In other embodiments, the first chamber may have other geometric shapes such as square, rectangular, round, pad-shaped, etc.

Figure 1D:
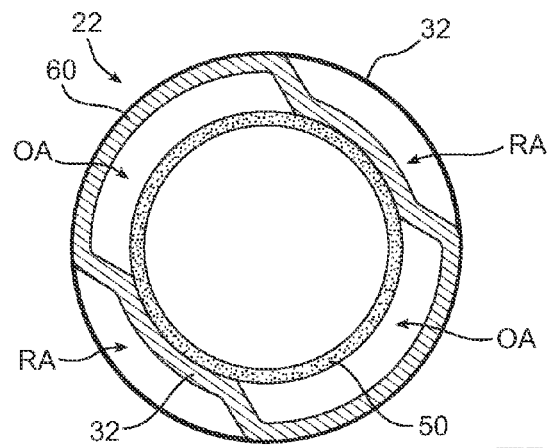
FIG. 1D shows a cross-sectional view of the implant shown in FIG. 1B taken along line 1D-1D thereof.
Figure 1E:
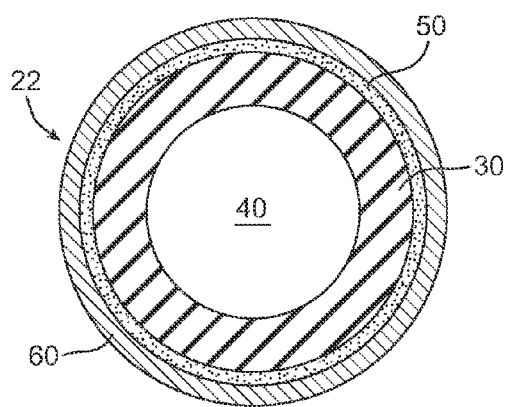
FIG. 1E shows a cross-sectional view of the implant shown in FIG. 1B taken along line 1E-1E thereof.

In one embodiment, in order to limit and/or prevent volume expansion of the first chamber 22 as fluid is introduced therein, a series of restraining elements 32, such as welds, are provided intermittently along the length of the first chamber 22. FIG. 1D shows a cross-sectional view of the first chamber 22 taken along line 1D-1D of FIG. 1B. As shown in FIG. 1D, in one embodiment, the restraining element 32 is formed by pinching opposing surfaces of the flexible outer layer 60 and the inner layer 50 together and joining the opposing surfaces together to form a restricted area RA of the first chamber that limits fluid flow. In one embodiment, fluid is only free to flow through the open areas of the first chamber designated OA. FIG. 1E shows a cross-sectional view of the first chamber 22 taken along line 1E-1E of the FIG. 1B. The second conduit 30 has a central channel 40 that provides fluid to the first chamber 22. The inner layer 50 is attached to the distal end of the second conduit and extends distally of the second conduit. The outer layer 50 surrounds the inner layer 60 and also preferably extends beyond the second conduit 30. A gap (not shown in FIG. 1E) desirably extends between the inner and outer flexible layers 50, 60 for enabling fluid to flow into the first chamber 22.

The restraining elements 32 shown in FIGS. 1C and 1D are preferably formed intermittently along the length of the first chamber 22. As noted above, the restraining elements 32 weld opposing surfaces of the inner and outer layers 50, 60 together so as to provide a restricted area RA for fluid flow and to prevent volume expansion of the first chamber 22 in the vicinity of the restraining elements. The restraining elements 32 cooperatively prevent and/or limit volume expansion of the first chamber as fluid is introduced through the second conduit 30 and into the first chamber. As a result, when fluid is introduced into the first chamber 22, the rigidity, shape, and/or length of the first chamber 22 will change, however, the volume or cross-sectional dimension of the first chamber 22 will not increase appreciably.

Although the present invention is not limited by any particular theory of operation, it is believed that providing one or more restraining elements 32 along the length of a first chamber will reduce the amount of fluid required to increase the rigidity, change the shape and/or lengthen the first chamber to achieve a therapeutic benefit. Because the first chamber 22 does not preferably expand in volume as fluid is introduced therein, significantly less fluid is required to change the shape of the first chamber and/or increase the rigidity of the first chamber than is required when using implants having single walled or expandable chambers.

Figure 2A:
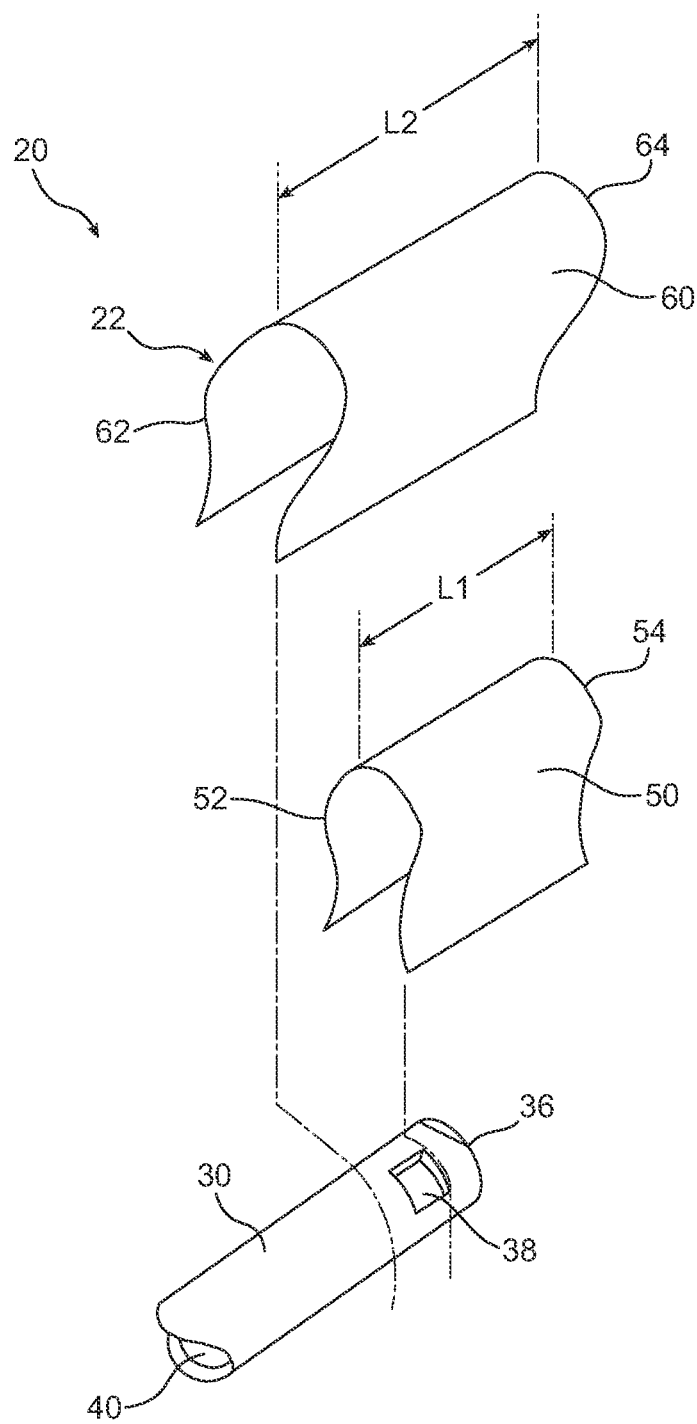
FIG. 2A shows an exploded view of an implant including a first chamber and a conduit for supplying fluid to the first chamber, in accordance with one embodiment of the present invention.
Figure 2B:
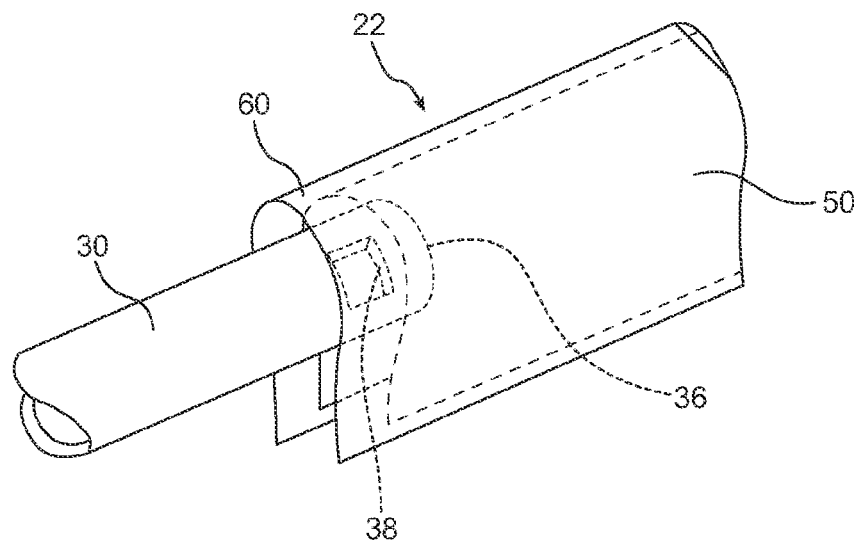
FIG. 2B shows a partially assembled view of the implant shown in FIG. 2A, in accordance with one embodiment of the present invention.
Figure 2C:
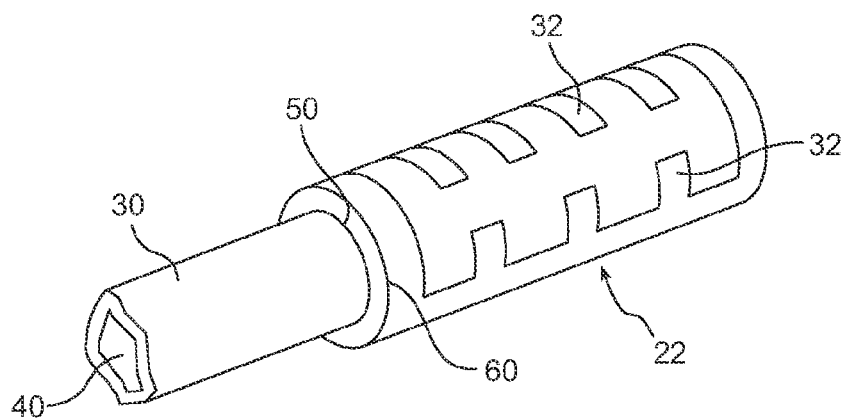
FIG. 2C shows a fully assembled view of the implant shown in FIGS. 2A and 2B, in accordance with one embodiment of the present invention.

FIGS. 2A-2C show a method of making the implant shown in FIGS. 1A and 1B, in accordance with one preferred embodiment of the present invention. Referring to FIG. 2A, in one embodiment, the implant 20 preferably includes the second conduit 30 having a closed distal end 36 and a radial opening 38 formed in the outer wall of the second conduit 30. The radial opening 38 may be located adjacent the distal end 36 of the second conduit 30. The second conduit 30 includes a central channel 40 adapted to pass fluid therethrough. As fluid is forced toward the distal end 36 of the second conduit 30, the fluid passes through the channel 40 and out of the radial opening 38. When it is desired to transform the implant from the more rigid state (FIG. 1B) to the more flexible state (FIG. 1A), the fluid is removed from the first chamber through the radial opening 38 and the fluid channel 40.

Referring to FIG. 2A, in one embodiment, the first chamber 22 of the implant 20 may be formed by securing a flexible inner layer 50 over the outer surface of the distal end 36 of the second conduit 30. The flexible inner layer 50 preferably has a proximal edge 52 and a distal edge 54. The proximal edge 52 is preferably secured to an outer surface of the second conduit 30 between a distal end of the radial opening 38 and the distal end 36 of the second conduit 30. The distal edge 54 of the flexible inner layer 50 preferably extends beyond the distal end 36 of the second conduit 30. In one embodiment, the flexible inner layer 50 is preferably wrapped around the outer surface of the second conduit 30 to form an inner layer having a cylindrical shape. The proximal edge 52 of the flexible inner layer 50 is preferably secured to the outer surface of the second conduit 30 so as to form a fluid-tight seal therewith.

The first chamber 22 also preferably includes a flexible outer layer 60 having a proximal edge 62 and a distal edge 64. The flexible outer layer 60 preferably overlies the flexible inner layer 50. In one embodiment, the proximal edge 62 of the flexible outer layer 60 is preferably attached to the outer surface of the second conduit 30 at a location that is proximal to the radial opening 38. The flexible outer layer 60 is preferably wrapped around the flexible inner layer 50 and the distal end 36 of the second conduit 30 to form a cylindrical-shaped structure. The distal edge 64 of the flexible outer layer 60 is preferably secured to the distal edge 54 of the inner layer 50 for forming a fluid-tight seal therewith.

Referring to FIG. 2A, in one embodiment, the flexible inner layer 50 has a first length $L_1$ and the flexible outer layer 60 has a second length $L_2$ that is greater than the first length $L_1$. Referring to FIGS. 2A and 2B, in one embodiment, the inner layer 50 and the outer layer 60 are assembled over the distal end 36 of the second conduit 30. The respective distal edges 54, 64 of the inner and outer layers 50, 60 are preferably secured together to form a fluid-tight seal. The proximal edge 52 of the inner layer 50 is secured to the outer surface of the second conduit 30 at a location that is distal to the radial opening 38, and the proximal edge 62 of the outer layer 60 is preferably secured to the outer surface of the second conduit 30 at a location that is proximal to the radial opening 38. The fluid that passes through the radial opening 38 desirably fills the gap between the inner and outer layers 50, 60 for filling the first chamber 22.

Referring to FIG. 2C, in one embodiment, the outer perimeters of the inner and outer layers 50, 60 are preferably bonded together to form a sealed first chamber 22 between the inner and outer layers, and the lower edges of the joined layers are bonded together to form a cylindrical-shaped device. The formation of a dual-walled cylindrical-shaped element enables the rigidity and shape of the implant to be modified while using less fluid than is required for implants having single walled construction or expandable chambers. In one embodiment, the inner and outer layers are intermittently joined together via restraining elements 32 such as spot welds that are adapted to prevent and or substantially limit expansion of the first chamber 22 as fluid is introduced into the first chamber. In one embodiment, providing a series of restraining elements 32 enables the rigidity, shape and/or length of the first chamber 22 to be modified as fluid is introduced into the first chamber with minimal or no expansion to the volume of the first chamber. In other embodiments, the first chamber may have a corrugated or "honey-combed" interior structure that enables a smaller volume of fluid to be used for transforming the first chamber from a more flexible state to a more rigid state. Although the present invention is not limited by any particular theory of operation, it is believed that these preferred designs require less fluid than is required for increasing the rigidity of an expandable or hollow structure such as a balloon or a pouch. As such, the present invention provides an implant that is easier to transform from a more flexible state to a more rigid state and requires a significantly smaller fluid reservoir to supply fluid for the transformation.

Referring to FIGS. 2B and 2C, in one embodiment, fluid is forced through the elongated channel 40 and toward the distal end 36 of the second conduit 30. As the fluid reaches the distal end 36 of the second conduit 30, the fluid passes through the radial opening 38 and fills a space or gap between the inner layer 50 and the outer layer 60. As the fluid pressure increases within the space between the inner and outer layers 50, 60, the first chamber 22 becomes more rigid, straighter, and/or lengthens. As noted herein, the use of the two layer design and the restraining elements 32 minimizes the volume of fluid required to change the rigidity and/or shape of the first chamber 22 so that less fluid is needed to transform the first chamber from a more flexible state to a more rigid state.

Figure 3A:
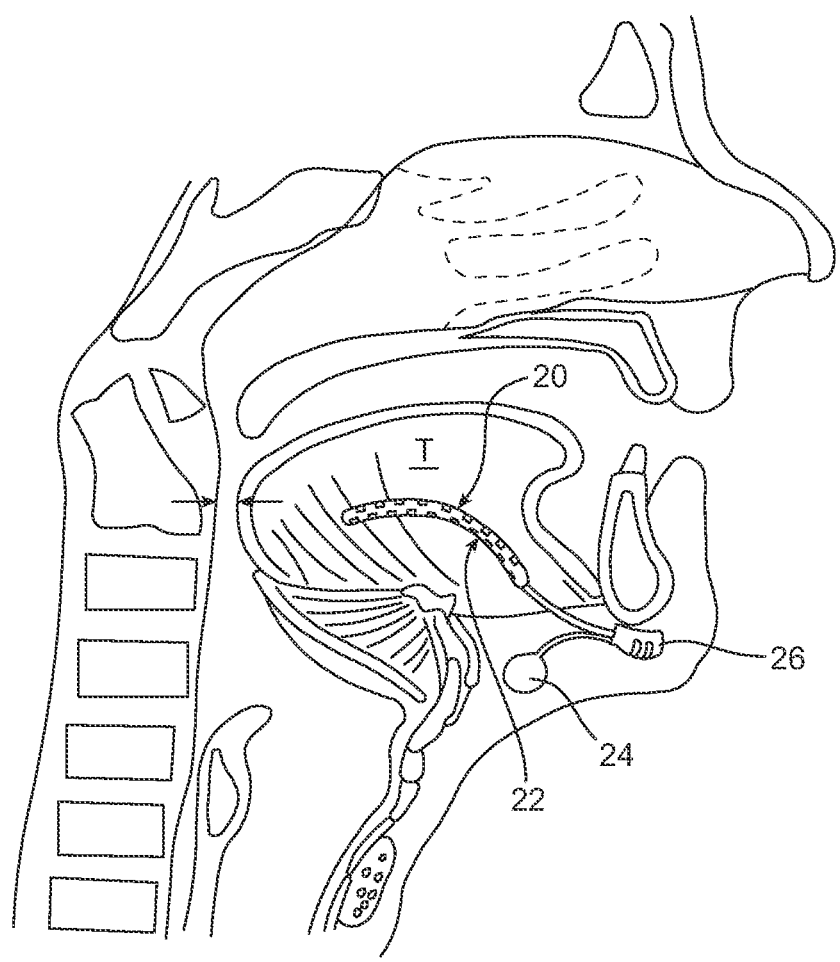
FIG. 3A shows the implant of FIGS. 1A-1B disposed in soft tissue for treating obstructive sleep apnea, in accordance with one embodiment of the present invention.
Figure 3B:
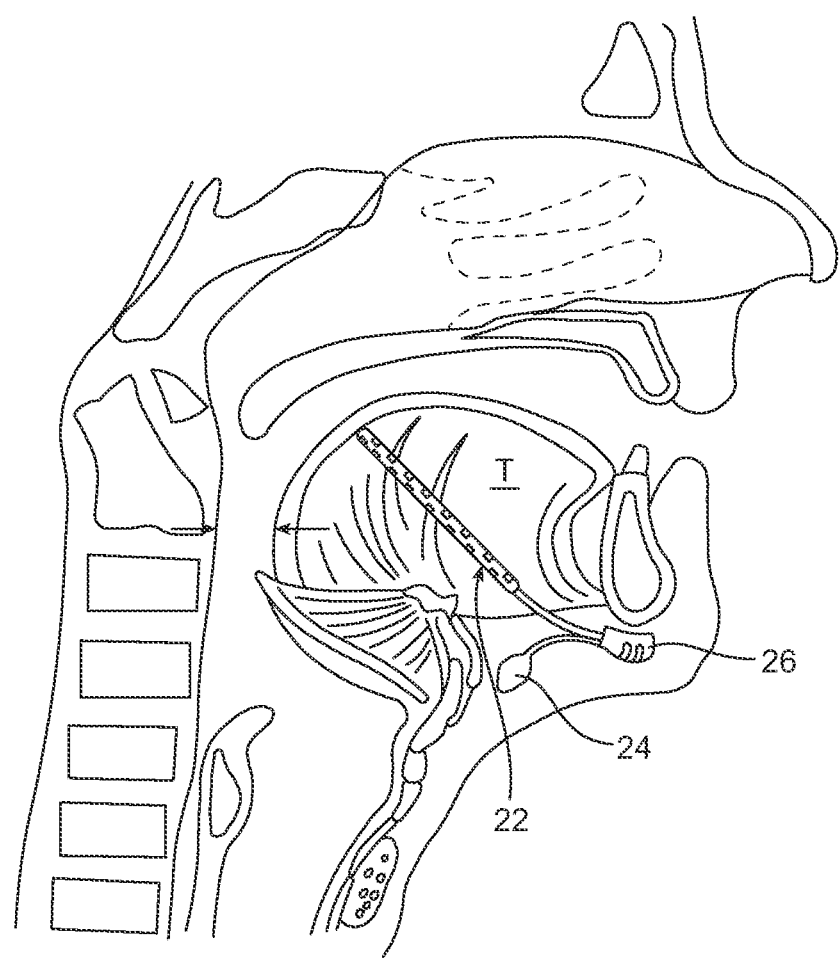
FIG. 3B shows the implant of FIG. 3A after fluid has been transferred into the first chamber for transforming the first chamber into a more rigid state and straighter, in accordance with one embodiment of the present invention.

In one embodiment, the implant shown and described herein may be used for treating obstructive sleep apnea. Referring to FIG. 3A, in one embodiment, the first chamber 22 of the implant is implantable in a tongue T, and the second chamber 24 and the fluid transfer assembly 26 are implantable in the infra-mandibular region of a patient. Referring to FIG. 3B, the fluid transfer assembly 26 may be selectively engaged by a patient for transferring fluid from the second chamber to the first chamber 22. As the first chamber 22 is pressurized by the fluid, the first chamber preferably becomes straighter and more rigid to change the shape of the tongue T and to provide support to the tongue T. As a result, posterior displacement of the tongue T is minimized and the resultant airway is enlarged, as shown by the tips of the arrows seen in FIG. 3B.

In one embodiment, the configuration of the implant 20 is preferably adapted to be controlled by a patient. When the patient is ready for sleep, the patient engages the fluid transfer assembly 26 located under the skin for introducing fluid into the first chamber 22 and transforming the first chamber 22 from the more flexible state shown in FIG. 3A to the more rigid state shown in FIG. 3B. In one embodiment, the fluid transfer assembly may require a patient to use manual pumping by squeezing a bulb. In another embodiment, the fluid transfer assembly 26 may be remotely operated through the skin using magnetic coupling or electric field energy. After fluid has been introduced into the first chamber, the patient will then sleep with the implant 20 in the more rigid, straighter configuration shown in FIG. 3B. Upon awakening, a patient may engage the fluid transfer assembly 26 so as to withdraw fluid from the first chamber 22 for reducing the rigidity of the first chamber 22. In the flexible or reduced pressure state shown in FIG. 3A, the tongue T is preferably able to move freely and is unaffected by the presence of the implant 20. Thus, in one embodiment, the implant 20 only affects the tongue T during sleep and the implant is not noticeable when the patient is awake so as to have no effect on speech or swallowing. In addition, because the implant is a pressurized cylinder fabricated from flexible materials, in the event that a patient has forceful swallowing during sleep, the implant may deform temporarily to allow swallowing. After the muscular activity associated with swallowing has ceased, the implant 20 returns to the preferred shape shown in FIG. 3B for supporting and shaping a relaxed tongue.

Figure 4:
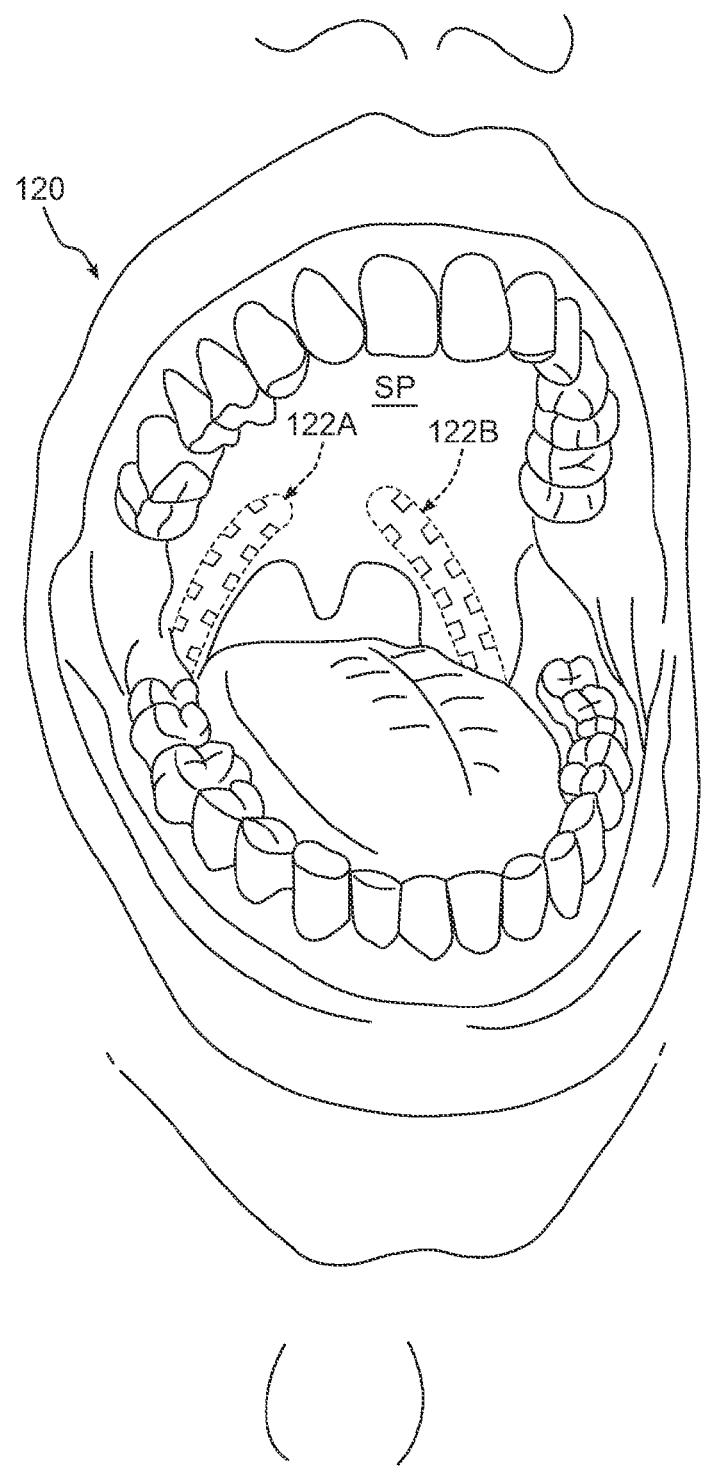
FIG. 4 shows a system for treating medical disorders including at least one implant disposed in a soft palate of a patient, in accordance with one embodiment of the present invention.

Referring to FIG. 4, in one embodiment, an implant 120 having one or more of the features described above is implantable within the soft tissues of the palate. The implant 120 may be used for treating various medical disorders including treating obstructive sleep apnea and snoring. In the particular embodiment shown in FIG. 4, the implant 120 preferably includes a pair of first chambers 122A, 122B positioned within a soft palate SP. The fluid pressure within the respective first chambers 122A, 122B may be increased for changing the shape and/or increasing the rigidity of the respective first chambers 122A, 122B, which, in turn, changes the shape and/or holds the shape of the soft palate SP. In the embodiment shown in FIG. 4, the fluid transfer assembly and the fluid reservoir element (not shown) are placed remotely from the location of the first chambers 122A, 122B. In one embodiment, the fluid transfer assembly and/or the fluid reservoir may be positioned within an inframandibular region of a patient. The fluid transfer assembly is preferably engageable through the skin or mucosal lining of the patient.

Figure 5:
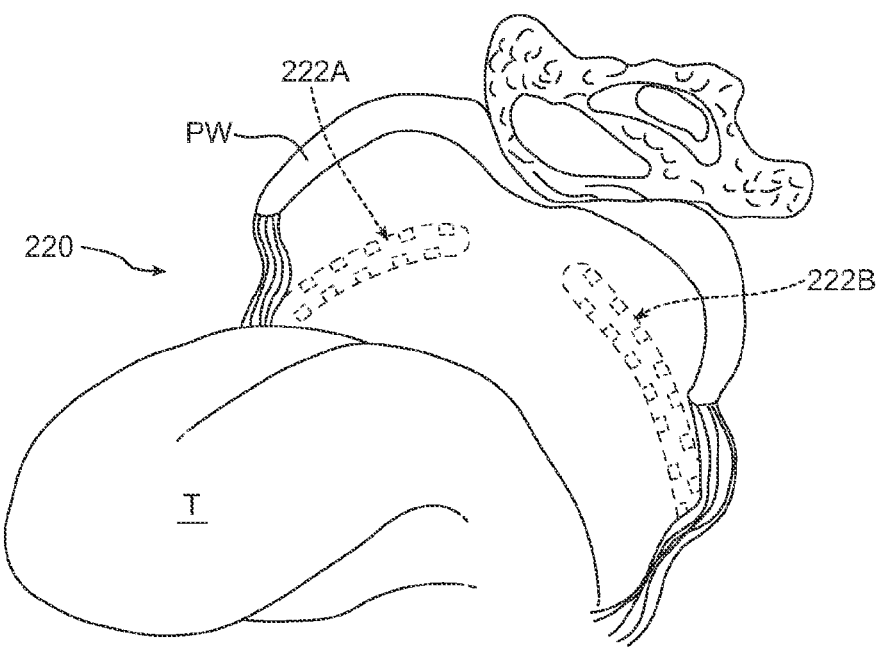
FIG. 5 shows a system for treating medical disorders including at least one implant disposed in a pharyngeal wall of a patient, in accordance with one embodiment of the present invention.

Referring to FIG. 5, in one embodiment, an implant having a structure as described herein is positioned within the pharyngeal wall PW of a patient. In one embodiment, the implant 220 preferably includes a pair of first chambers 222A, 222B that are implantable within the pharyngeal wall PW. The fluid reservoir(s) and the fluid transfer assembly(ies) for the first and second chambers 222A, 222B are preferably placed remotely from the location of the first chambers 222A, 222B, for example, in an inframandibular or mastoid region of a patient's neck. The implant shown in FIG. 5 may be used for treating medical disorders such as obstructive sleep apnea and dysphagia. Although the implants shown in the embodiment of FIG. 5 extend horizontally, the implants may also extend vertically or at any angle therebetween.

Figure 6:
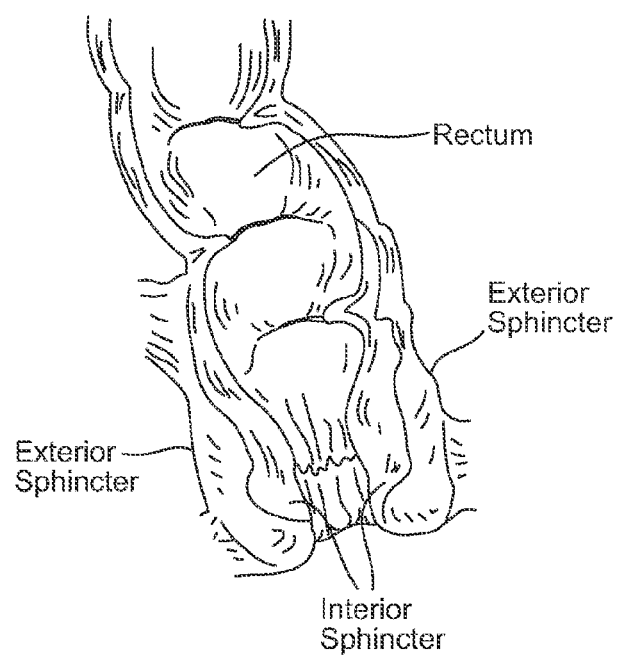
FIG. 6 shows a cross-sectional view of a normal rectum and anal sphincter.

In one embodiment, the implant disclosed herein may be used for treating anal or fecal incontinence or rectal prolapse. FIG. 6 shows a normal bowel including a rectum, an interior sphincter, and an exterior sphincter. The bowel of a patient may develop a number of disorders including improper angular orientation, kinking or twisting. In one embodiment, the implant disclosed herein may be used to alleviate the symptoms associated with angular orientation, twisting and kinking of the bowel.

Figure 7A:
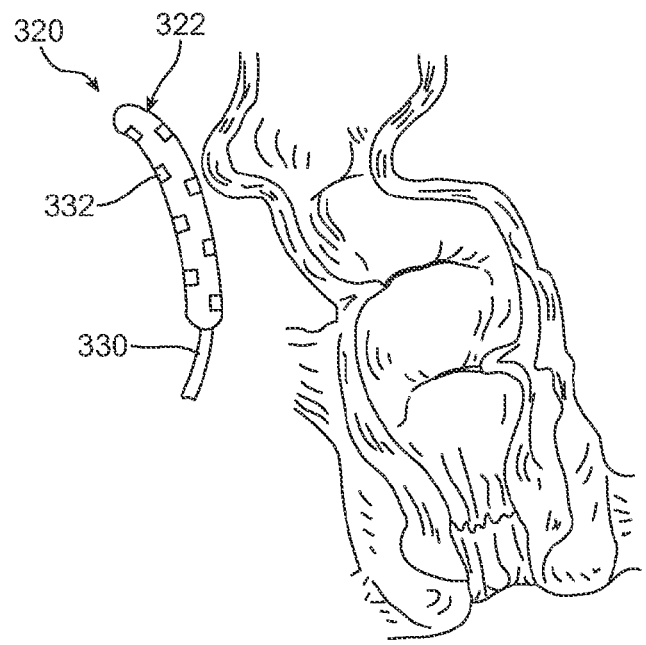
FIGS. 7A and 7B show an implant used for treating anal incontinence, in accordance with one embodiment of the present invention.

Referring to FIG. 7A, in one embodiment, an implant 320 includes a first chamber 322 that is adapted to receive a fluid such as a liquid or a gas. The first chamber 322 is coupled with a conduit 330 that selectively supplies the fluid to the first chamber 322. The first chamber 322 includes one or more restraining elements 332 such as welds that are formed along the length thereof for preventing and/or restraining volume expansion of the first chamber 322 as fluid is introduced into the first chamber. The first chamber 322 preferably includes a flexible outer layer that enables the first chamber to transform from a more flexible state when fluid is removed from the first chamber to a straighter, more rigid state when fluid is introduced into the first chamber.

Figure 7B:
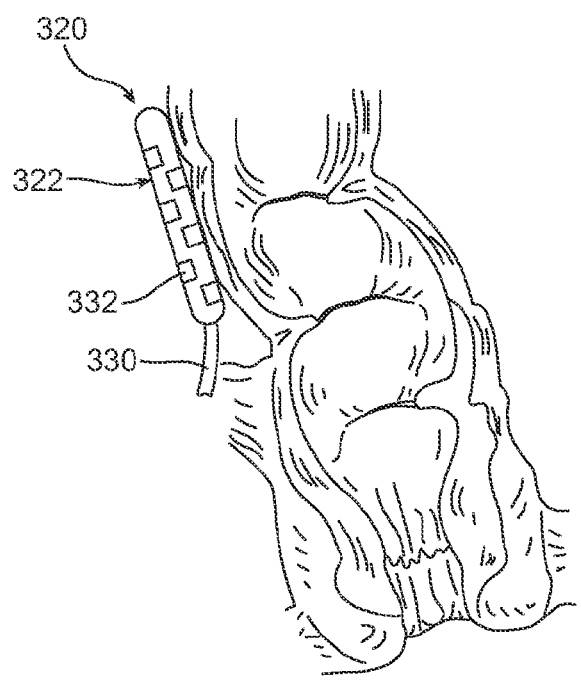

In the embodiment shown in FIG. 7A, the first chamber 322 of the implant 320 is disposed adjacent a kink formed in a patient's rectum. In FIG. 7A, fluid has been withdrawn from the first chamber so that the first chamber is flexible and has a curved configuration. Referring to FIG. 7B, in one embodiment, in order to remove the kink from the rectum and return it to the normal configuration shown in FIG. 6, fluid is introduced into the first chamber 322 of the implant 320. As the fluid is introduced into the first chamber 322, the first chamber straightens and becomes more rigid. In one embodiment, the one or more restraining elements 332 provided along the length of the first chamber 322 prevent the volume of the first chamber from expanding. As the first chamber 322 straightens and becomes more rigid, the outer surface of the first chamber forces the kink in the rectum to move inwardly, which removes the kink and returns the rectum to the normal configuration shown in FIG. 6.

Although the present invention is not limited by any particular theory of operation, it is believed that providing one or more restraining elements 322 along the length of the first chamber 322 minimizes the volume of fluid that will be required to transform the implant from the more flexible configuration shown in FIG. 7A to the more rigid, straighter configuration shown in FIG. 7B. As a result, the overall implant system may be more compact and not require as large a fluid reservoir or pumping mechanism as is required in prior art devices having expandable chambers. Moreover, because less fluid is required to transform the first chamber of the implant, a patient will spend less time transferring fluid from the fluid reservoir to the first chamber 322, which will enable a patient to attain a therapeutic benefit in a more efficient manner.

In one embodiment, a patient may activate the implant 320 immediately prior to a bowel movement by engaging the pumping mechanism to transfer the fluid from the fluid reservoir to the first chamber. After the patient has completed the bowel movement, the patient may engage the pumping or valving mechanism to remove the fluid from the first chamber 322 and return the fluid to the fluid reservoir. As a result, the first chamber will transform back from the rigid, straight configuration shown in FIG. 7B to the more flexible, curved configuration shown in FIG. 7A.

Figure 8:
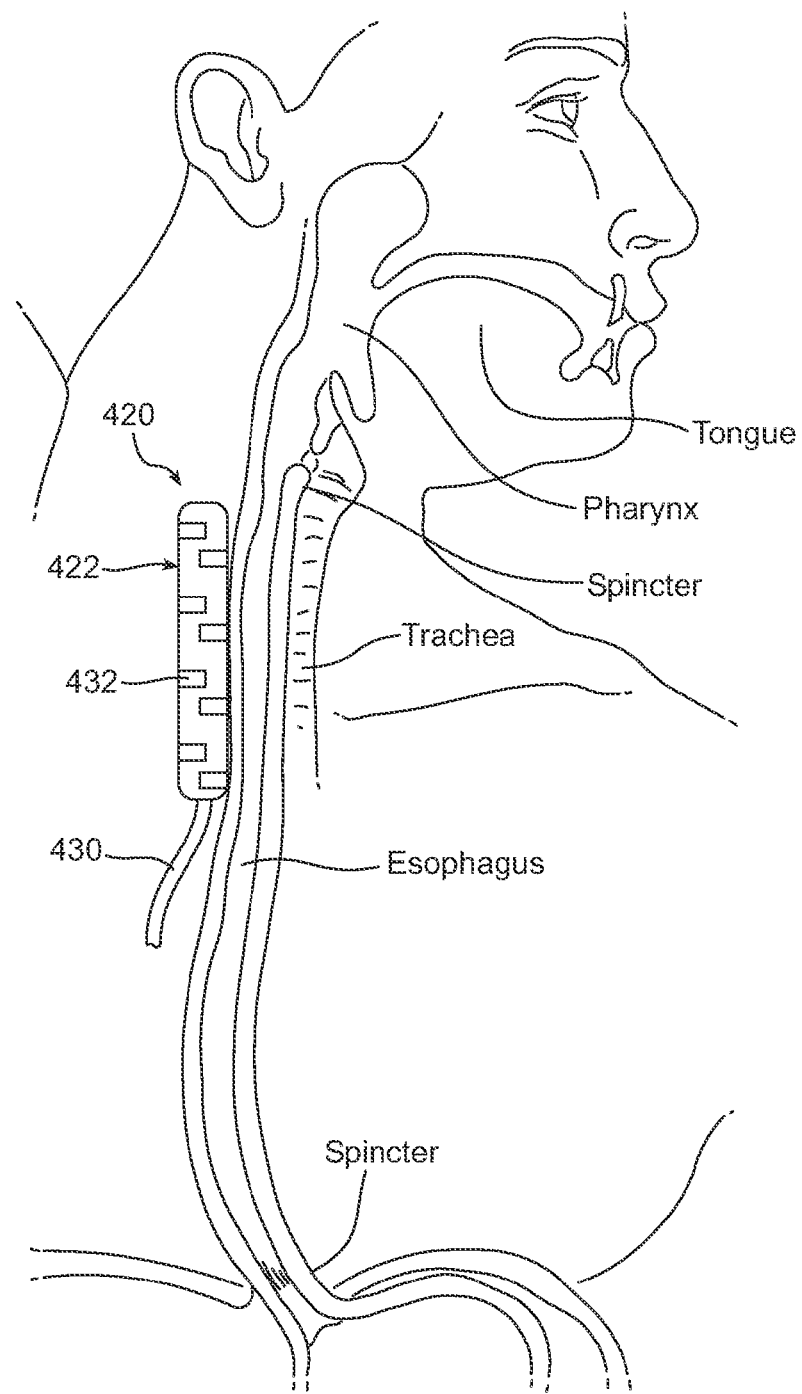
FIG. 8 shows an implant used for treating dysphagia, in accordance with one embodiment of the present invention.

Referring to FIG. 8, in one embodiment, a fluid-filled implant as disclosed herein may be used for treating difficulties associated with swallowing such as dysphagia, which occurs when there is a problem with any part of the swallowing process. In one embodiment, an implant 420 as disclosed herein is positioned adjacent the trachea of a patient. The implant 420 preferably includes a first chamber 422 and a conduit 430 that is adapted to supply fluid to the first chamber. The first chamber 422 includes a plurality of restraining elements 432 formed along the length thereof that prevent volume expansion of the first chamber 422 as fluid is introduced therein. In a first state, the first chamber 422 is devoid of fluid so that the first chamber remains flexible and may have a substantially curved configuration. When it is desired to facilitate swallowing in a patient, fluid may be introduced into the first chamber 422 through the fluid conduit 430. As the fluid is introduced into the first chamber 422, the first chamber becomes more rigid and straighter to assume the configuration shown in FIG. 8. The plurality of restraining elements 432 provided along the length of the first chamber prevent volume expansion of the first chamber as the fluid is introduced therein. Thus, the first chamber may be transformed into a therapeutic configuration using less fluid than is required with prior art implants that have expandable elements. As the patient eats, the first chamber 422 is preferably maintained in the more rigid, straighter configuration shown in FIG. 8 to support swallowing. When the patient has completed eating, the fluid may be withdrawn from the first chamber 422 so that the first chamber returns to a more flexible configuration. The patient may selectively transform the first chamber between the more flexible and more rigid configuration by selectively introducing and removing the fluid from the first chamber by engaging a pump and/or valve assembly disposed subcutaneously.

Figure 9:
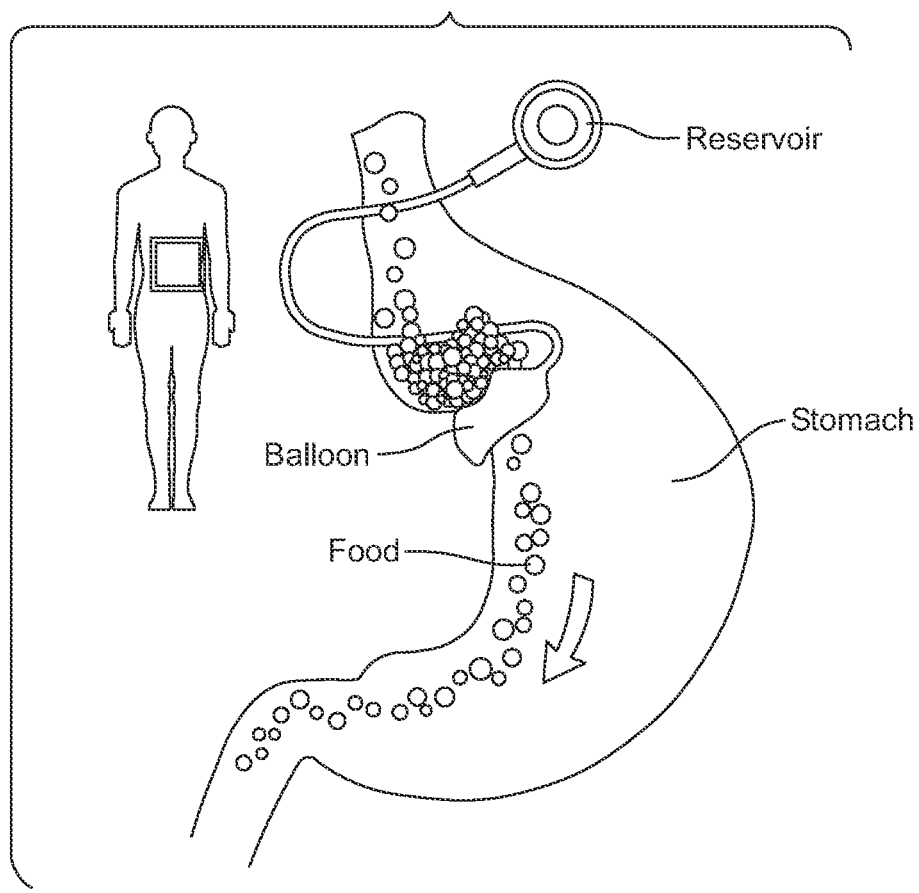
FIG. 9 shows a prior art stomach band implant used for treating an eating disorder.

FIG. 9 shows a prior art stomach banding device including an inflatable balloon that is coupled with a fluid reservoir. When it is desirable to provide a patient with a "full" feeling to encourage less eating, the fluid in the reservoir may be transmitted to the expandable balloon for inflating the balloon. As the balloon is inflated, the balloon pushes against an underside of the small stomach pouch. As the patient eats food, the inflated balloon retains the food for a longer period of time within the small stomach pouch for giving the patient a full feeling, which will desirably cause the patient to eat less food. One drawback with the prior art implant shown in FIG. 9 is that the balloon is expandable, thereby requiring substantially more fluid for attaining a therapeutic benefit.

Figure 10A:
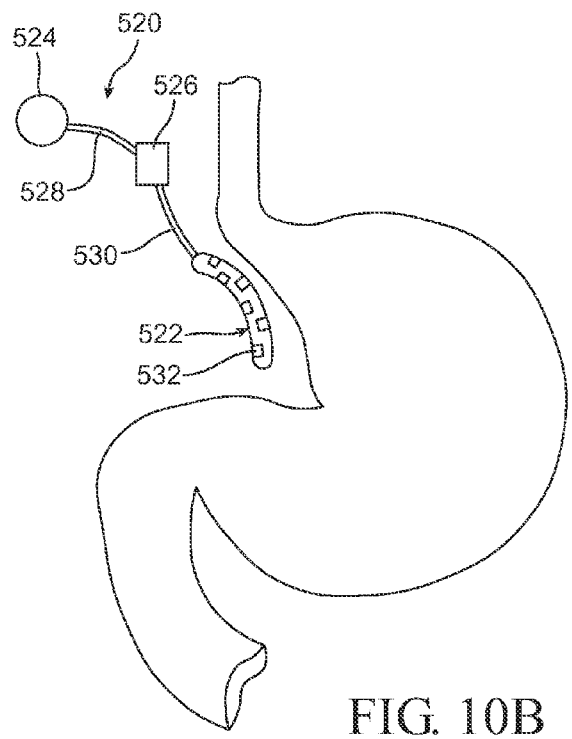
FIGS. 10A and 10B show an implant used for treating an eating disorder, in accordance with one embodiment of the present invention.
Figure 10B:
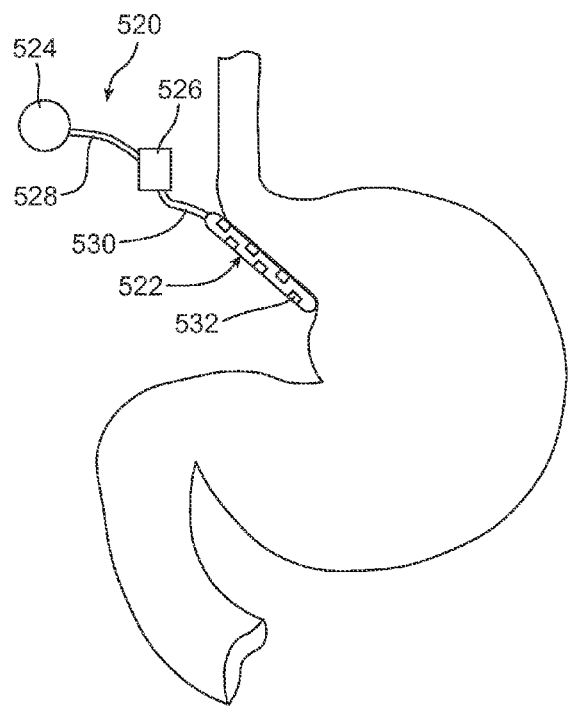

FIGS. 10A and 10B show an implant device that attains a therapeutic benefit for treating eating disorders while using less fluid. As a result, the overall size of the system may be reduced and a therapeutic benefit may be attained by a patient in a more efficient manner. Referring to FIG. 10A, in one embodiment, a fluid filled implant system 520 similar to that described in more detail herein includes a first chamber 522, a second chamber 524 that functions as a fluid reservoir, a fluid transfer assembly 526 for transferring the fluid between the reservoir 524 and the first chamber 522, and first and second conduits 528, 530 that couple the fluid reservoir 524 with the first chamber 522.

In one embodiment, the implant 520 is disposed adjacent the small stomach pouch of a patient. In FIG. 10A, the first chamber 522 is devoid of fluid so that the first chamber maintains a more flexible, substantially curved configuration. Referring to FIG. 10B, in one embodiment, the fluid is transmitted from the fluid reservoir 524 to the first chamber 522 to transform the first chamber to a more rigid, straighter configuration. As the first chamber 522 becomes more rigid and straighter, the outer surface of the first chamber abuts against the small stomach pouch for pushing the small stomach pouch inwardly so as to reduce the volume of the patient's small stomach pouch. The first chamber 522 preferably includes a plurality of restraining elements 532, such as welds, that minimize volume expansion of the first chamber as the fluid is introduced therein. As a result, the first chamber may be transformed into its therapeutic configuration in a more efficient manner and while using less fluid. In the configuration shown in FIG. 10B, a patient will more quickly attain a "full" feeling when eating than when the implant is in the configuration shown in FIG. 10A.

In one embodiment, prior to eating, a patient may transform the first chamber 522 from the configuration shown in FIG. 10A to the configuration shown in FIG. 10B. The patient will maintain the first chamber 522 in the configuration shown in FIG. 10B while eating. Later, preferably after eating, the patient may remove the fluid from the first chamber 522 by engaging the pump 526 for returning the fluid to the fluid reservoir 524.

Figure 11A:
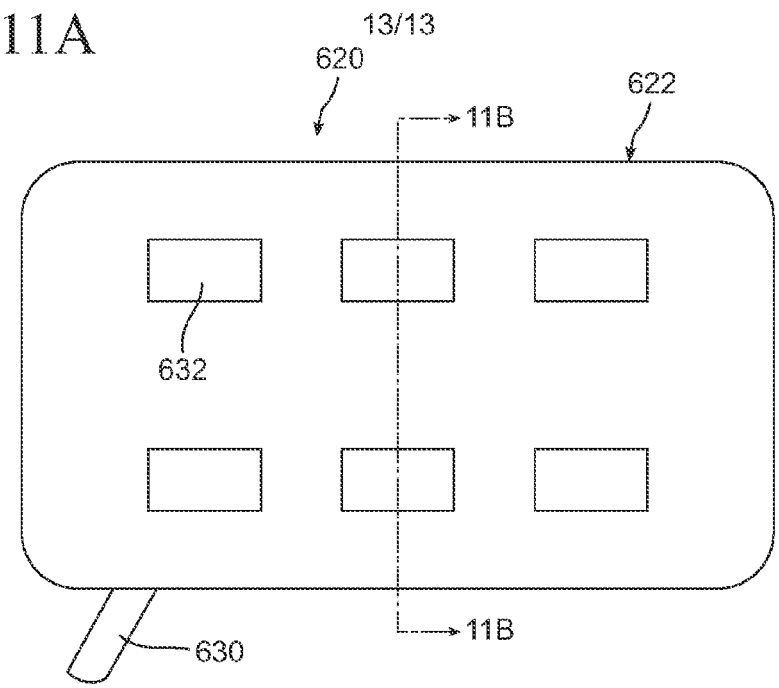
FIG. 11A shows a top plan view of an implant for treating medical disorders, in accordance with one embodiment of the present invention.

In one embodiment, the implant disclosed herein has a first chamber or working end that has a substantially cylindrical shape. In other embodiments, the implant may have any geometric shape including a spherical, square, rectangular or dome shaped appearance. Referring to FIG. 11A, in one embodiment, the implant 620 has a substantially rectangular shaped configuration when viewed from the top. As such, the implant may be a pad that covers a larger surface area than a cylindrical shaped implant. The implant 620 preferably includes a first chamber 622 that is adapted to receive a fluid. The first chamber 622 is coupled with a fluid conduit 630 that is used for introducing fluid into the first chamber 622 and removing fluid from the first chamber. The first chamber 622 desirable includes a plurality of restraining elements 632 formed therein that are adapted to minimize or prevent volume expansion of the first chamber as fluid is introduced therein. In one embodiment, the first chamber 622 is made of a flexible film and the restraining elements 632 are formed by welding opposing surfaces of the flexible film together to permanently join the opposing surfaces.

Figure 11B:
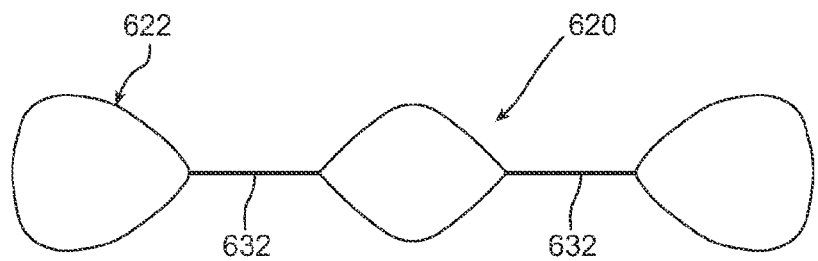
FIG. 11B shows a cross-section view of the implant shown in FIG. 11A taken along line 11B-11B thereof.

FIG. 11B shows a cross-sectional view of the implant 620 shown in FIG. 11A. As shown in FIG. 11B, the restraining elements 632 are preferably joined together. The fluid introduced into the first chamber 622 preferably flows around the restraining elements. The restraining elements are adapted to substantially limit or prevent volume expansion of the first chamber 622 as fluid is introduced therein. As a result, when fluid is introduced therein, the first chamber 622 will preferably become more rigid and straighter, however, the volume of the first chamber will not increase or will not increase substantially.

Figure 12:
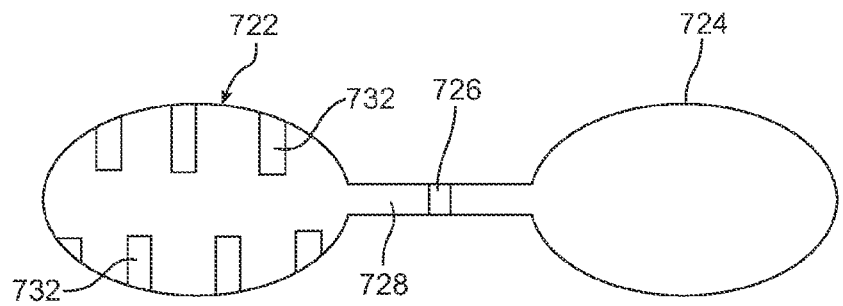
FIG. 12 shows an implant for treating medical disorders, in accordance with one embodiment of the present invention.

Referring to FIG. 12, in one embodiment, an implant 720 for treating medical disorders such as obstructive sleep apnea includes a first chamber 722 desirably implantable within soft tissue and a second chamber 724 preferably implantable within a patient. The first chamber 722 and the second chamber 724 are desirably in fluid communication with one another via a fluid transfer assembly extending therebetween. The fluid transfer assembly desirably includes a fluid conduit 728 that preferably includes a pump or a valve 726, such as a duck-bill valve, that enables fluid to be transferred back and forth between the first chamber 722 and the second chamber 724. The valve 726 may be engaged by a patient for transferring fluid, such as saline solution, between the second chamber and the first chamber so as to modify the rigidity, flexibility, and/or shape of the first chamber. In one embodiment, the implant 720 shown in FIG. 12 is a unitary structure that has a single seam located around the outer perimeter of the implant. In one embodiment, the first chamber 722, the second chamber 724, and the fluid conduit 728 may comprise two flexible films that are joined together around the perimeter of the films. The pump or valve 726 may be disposed between the two joined flexible films for controlling the flow of fluid between the first chamber and the second chamber. The first chamber 722 preferably includes one or more restraining elements 732 as described above for preventing or limiting volume expansion of the first chamber as the fluid is introduced into the first chamber to provide the benefits discussed herein.

Although the present invention is not limited by any particular theory of operation, it is believed that the implants disclosed herein may be utilized to provide favorable support and reshaping of soft tissue upon demand from a patient. Since the implant devices of the present invention are fabricated from flexible film materials, the implant devices are preferably less noticeable or not noticeable when the patient is awake. In certain preferred embodiments of the present invention, the implant is formed of flexible films. In one embodiment, the fluid transfer assembly may be included in-line with two layers of film that have been thermo-formed into a bladder shape on one end and bonded together on the opposing end to provide a "unitary" type construction without requiring extra bonding, seams or joints.

In one embodiment, the implant may have an outer surface that encourages tissue in-growth so as to stabilize the implant within the tissue and so as to minimize the opportunity for tissue erosion. The outer surface modification may be achieved by texturizing the outer surface, making the implant porous through the addition of holes (e.g. drilled or pierced holes), encapsulating the implant with a braided, surgical mesh, or fleece type material, and/or coating the implant with bone growth stimulating agents such as hydroxyapatite.

The present invention provides a number of advantages over prior art implants, devices and methods used for treating medical disorders. First, the implant disclosed herein provides for simple surgical procedures that are minimally invasive. In addition, the implants disclosed herein provide both immediate and long term results for treating medical disorders such as treating obstructive sleep apnea syndrome and hypopnea. Moreover, the implants disclosed herein do not require a significant level of patient compliance. The present invention also preferably uses materials having long-term biocompatibility.

Although various embodiments disclosed herein relate to use in humans, it is contemplated that the present invention may be used in all mammals. Moreover, the methods, systems and devices disclosed herein may incorporate any materials that are biocompatible, as well as any solutions or components that minimize rejection, enhance tissue ingrowth, enhance the formation of mucosal layers, and improve acceptance of the device by a body after the device has been implanted.

The present application may incorporate one or more of the features disclosed in commonly assigned U.S. patent application Ser. Nos. 12/182,402, filed Jul. 30, 2008; 12/183,955, filed Jul. 31, 2008; 12/257,563, filed Oct. 24, 2008; 12/261, 102, filed Oct. 30, 2008; and 12/325,350, filed Dec. 1, 2008; and U.S. Patent Appln. Pub. Nos. 2007/0005109 and 2007/0005110, the disclosures of which are hereby incorporated by reference herein.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. An implant for treating medical disorders comprising:
a first chamber having a flexible outer layer;
a second chamber remote from first chamber, said second chamber being in communication with said first chamber;
a fluid transfer assembly remote from said first chamber for transferring fluid between said second chamber and said first chamber for selectively modifying the rigidity of said first chamber, wherein said first chamber, said second chamber, and said fluid transfer assembly comprise a unitary structure; and
at least one restraining element in contact with said flexible outer layer of said first chamber for restricting volume expansion of said first chamber when the fluid is transferred into said first chamber.

2. The implant as claimed in claim 1, wherein said first chamber becomes more rigid as the fluid is transferred into said first chamber and less rigid as the fluid is removed from said first chamber.

3. The implant as claimed in claim 1, wherein said first chamber is adapted to become more rigid and straighten as the fluid is transferred into said first chamber.

4. The implant as claimed in claim 1, wherein said first chamber is adapted to become more rigid and lengthen as the fluid is transferred into said first chamber.

5. The implant as claimed in claim 1, further comprising a first conduit extending between said second chamber and said fluid transfer assembly and a second conduit extending between said fluid transfer assembly and said first chamber for extracting the fluid from said second chamber and transferring the fluid through said first conduit, said fluid transfer assembly, and said second conduit, and into said first chamber.

6. The implant as claimed in claim 1, wherein said first chamber includes a flexible inner layer, and wherein said at least one restraining element comprises at least one weld joining opposing surface areas of said flexible inner and outer layers for forming said at least one restraining element.

7. The implant as claimed in claim 6, wherein said at least one weld restricts volume expansion of said first chamber in the vicinity of said at least one weld as the fluid is transferred into said first chamber.

8. The implant as claimed in claim 6, wherein said at least one weld comprises a plurality of welds joining respective opposing surface areas of said flexible outer layer, and wherein said plurality of welds are spaced from one another.

9. The implant as claimed in claim 1, wherein said first chamber is implantable within soft tissue of a patient at any selected angle relative to an anterior-posterior, lateral, vertical, or horizontal axis of the patient.

10. The implant as claimed in claim 1, wherein said first chamber is implantable within a tongue, a soft palate, a pharyngeal wall, or adjacent a rectum, a trachea, or a stomach.

11. The implant as claimed in claim 1, wherein the fluid comprises a liquid, a gas, or a combination thereof.

12. An implant for treating medical disorders comprising:
a first chamber;
a second chamber remote from said first chamber, said second chamber being in fluid communication with said first chamber;
a fluid transfer assembly coupling said first and second chambers, said fluid transfer assembly being remote from said first chamber and being adapted to transfer fluid therebetween for selectively modifying the rigidity of said first chamber, wherein said first chamber is adapted to become more rigid as the fluid is transferred into said first chamber, and wherein said first chamber, said second chamber, and said fluid transfer assembly comprise a unitary structure; and
at least one restraining element in contact with said first chamber for restricting expansion of said first chamber as the fluid is transferred into said first chamber.

13. The implant as claimed in claim 12, further comprising a first conduit extending between said second chamber and said fluid transfer assembly and a second conduit extending between said fluid transfer assembly and said first chamber for extracting the fluid from said second chamber and transferring the fluid through said first conduit, said fluid transfer assembly, and said second conduit to said first chamber.

14. The implant as claimed in claim 13, wherein said first chamber comprises a flexible layer covering a distal end of said second conduit.

15. The implant as claimed in claim 14, wherein said at least one restraining element comprises at least one weld in contact with said flexible layer for restricting volume expansion of said first chamber as the fluid is transferred into said first chamber.

16. The implant as claimed in claim 15, wherein said at least one weld prevents volume expansion of said first chamber as the fluid is transferred into said first chamber.

17. An implant for treating medical disorders comprising:
a first chamber including a flexible outer layer;
a second chamber remote from and in communication with said first chamber;
a fluid transfer assembly for selectively transferring fluid between said first and second chambers, said fluid transfer assembly being remote from said first chamber, wherein said first chamber is adapted to become more rigid as the fluid is transferred into said first chamber, wherein the flexible outer layer of said first chamber defines a volume that is non-expandable as the fluid is transferred into said first chamber, and wherein said first chamber, said second chamber, and said fluid transfer assembly comprise a unitary structure.

18. The implant as claimed in claim 17, further comprising at least one restraining element in contact with said first chamber for at least partially restricting volume expansion of said first chamber as the fluid is transferred into said first chamber.

19. The implant as claimed in claim 18, wherein said at least one restraining element comprises a plurality of spaced welds joining opposing surfaces of said flexible outer layer together.

20. The implant as claimed in claim 18, further comprising an elongated conduit in communication with said first chamber for supplying the fluid to said first chamber, wherein said at least one restraining element comprises at least one weld coupling said flexible outer layer with an outer surface of said elongated conduit.

21. The implant as claimed in claim 18, wherein said at least one restraining element comprises a plurality of restraining elements in contact with said flexible outer layer for preventing volume expansion of said first chamber as the fluid is transferred into said first chamber.

22. The implant as claimed in claim 17, further comprising:
a first conduit extending between said second chamber and said fluid transfer assembly; and
a second conduit extending between said fluid transfer assembly and said first chamber, wherein said fluid transfer assembly is compressible for drawing the fluid from said second chamber and transferring the drawn fluid through said first and second conduits for introducing the drawn fluid into said first chamber.

23. The implant as claimed in claim 22, wherein said fluid transfer assembly comprises a pressure relief valve that is openable for removing the fluid from said first chamber and transferring the fluid in series through said second conduit, said fluid transfer assembly, and said first conduit, and back to said second chamber for reducing the rigidity of said first chamber.

24. The implant as claimed in claim 1, wherein said first and second chambers are non-concentric.

* * * * *